US012194513B2

(12) United States Patent
Hayakawa

(10) Patent No.: US 12,194,513 B2
(45) Date of Patent: Jan. 14, 2025

(54) CLEANING AND STERILIZING METHOD FOR ASEPTIC FILLING MACHINE AND ASEPTIC FILLING MACHINE

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 18/042,620

(22) PCT Filed: Sep. 8, 2021

(86) PCT No.: PCT/JP2021/033010
§ 371 (c)(1),
(2) Date: Feb. 23, 2023

(87) PCT Pub. No.: WO2022/065035
PCT Pub. Date: Mar. 31, 2022

(65) Prior Publication Data
US 2023/0356269 A1    Nov. 9, 2023

(30) Foreign Application Priority Data

Sep. 23, 2020   (JP) ................. 2020-158242

(51) Int. Cl.
*B08B 9/032* (2006.01)
*A61L 2/04* (2006.01)
(Continued)

(52) U.S. Cl.
CPC .............. *B08B 9/0325* (2013.01); *A61L 2/04* (2013.01); *A61L 2/28* (2013.01); *B67C 3/001* (2013.01);
(Continued)

(58) Field of Classification Search
CPC ... B08B 2209/032; B08B 9/0325; A61L 2/04; A61L 2/28; A61L 2202/11; A61L 2202/14; A61L 2202/17; B67C 3/001
See application file for complete search history.

(56) References Cited

U.S. PATENT DOCUMENTS

2015/0291406 A1    10/2015  Hayakawa et al.
2016/0121376 A1*    5/2016  Hayakawa ............ B08B 9/0325
                                                                422/3
(Continued)

FOREIGN PATENT DOCUMENTS

JP    S51-088646 A    8/1976
JP    2000-153245 A   6/2000
(Continued)

OTHER PUBLICATIONS

International Search Report and Written Opinion (Application No. PCT/JP2021/033010) dated Nov. 16, 2021.

*Primary Examiner* — Douglas Lee
(74) *Attorney, Agent, or Firm* — BURR PATENT LAW, PLLC

(57) ABSTRACT

In an aseptic filling machine including content supply piping for feeding a content to a filler via a heat sterilization portion, CIP and SIP of the inside of the content supply piping is performed by circulating a cleaning liquid, SIP is performed by heating the cleaning liquid to a required temperature for sterilization from the start of the CIP or during the CIP, the overall heat transfer coefficient of the heating piping is calculated, it is determined that the CIP is completed when the overall heat transfer coefficient calculated reaches a target value, temperatures are measured by a plurality of temperature sensors provided, a lowest temperature is selected from the measured temperatures, F values are calculated for the selected lowest temperature, the calculated (Continued)

F values are accumulated, and it is determined that the SIP is completed when the accumulated F value reaches a target value.

4 Claims, 6 Drawing Sheets

(51) Int. Cl.
*A61L 2/28* (2006.01)
*B67C 3/00* (2006.01)

(52) U.S. Cl.
CPC ........ *A61L 2202/11* (2013.01); *A61L 2202/14* (2013.01); *A61L 2202/17* (2013.01); *B08B 2209/032* (2013.01)

(56) References Cited

U.S. PATENT DOCUMENTS

| | | | |
|---|---|---|---|
| 2020/0277178 A1 | 9/2020 | Hayakawa et al. | |
| 2020/0339401 A1* | 10/2020 | Hayakawa | ................ A61L 2/18 |
| 2021/0347621 A1* | 11/2021 | Kuwano | ............... B08B 9/0325 |

FOREIGN PATENT DOCUMENTS

| | | | | |
|---|---|---|---|---|
| JP | 2007-022600 A | 2/2007 | | |
| JP | 2007-331801 A | 12/2007 | | |
| JP | 2015-044593 A | 3/2015 | | |
| JP | 2019-064722 A | 4/2019 | | |
| JP | 2020-070067 A | 5/2020 | | |
| WO | 2014/103787 A1 | 7/2014 | | |
| WO | 2019/142742 A1 | 7/2019 | | |
| WO | WO-2020090733 A1 * | 5/2020 | ............. B08B 9/027 | |

* cited by examiner

CLEANING AND STERILIZING METHOD FOR ASEPTIC FILLING MACHINE AND ASEPTIC FILLING MACHINE

TECHNICAL FIELD

The present disclosure relates to a cleaning and sterilizing method for an aseptic filling machine that fills a container such as a PET bottle with a drink, and the aseptic filling machine.

BACKGROUND ART

When an aseptic filling machine fills a container such as a bottle with a drink, the drink itself has to be sterilized to be aseptic. In addition, CIP (Cleaning in Place) for cleaning the inside of drink supply piping and SIP (Sterilizing in Place) for sterilizing the inside of the drink supply piping have to be performed to make the inside of the drink supply piping aseptic, the drink supply piping being a path for feeding the drink to filling nozzles and including a surge tank, a liquid feeding pipe, a filler tank and the like. CIP and SIP of the drink supply piping of the aseptic filling machine are performed regularly or each time the kind of the drink is changed (see Patent Literatures 1, 2 and 3).

CIP is performed by passing a cleaning liquid containing water and an alkali agent such as caustic soda as an additive through a flow path from the pipe line of the drink supply piping to the filing nozzles of the aseptic filling machine and then passing a cleaning liquid containing water and an acid agent as an additive. This removes a residue of the previous drink in the drink supply piping, for example (see Patent Literatures 1, 2 and 3).

SIP is a process to sterilize the inside of the drink supply piping before the drink filling operation is started, and is performed by passing a heated steam or heated liquid through the drink supply piping cleaned by CIP, for example. This sterilizes the inside of the drink supply piping and makes it aseptic (see Patent Literature 3).

Typically, after CIP using a cleaning liquid is performed, the cleaning liquid is rinsed off, and then SIP is performed using a sterilizer or heated fluid. In this regard, it is proposed to perform CIP and SIP concurrently or in sequence by heating the cleaning liquid used for CIP to a temperature required for SIP (Patent Literature 4).

The cleaning liquid is passed to perform CIP, and when to determine that CIP is completed depends on the kind of the cleaning liquid. Conventionally, CIP is performed based on the temperature of the cleaning liquid and the time required for the cleaning empirically determined. As a result, the cleaning takes an unnecessary long time, which leads to a loss of time and energy. To address this problem, it is proposed to calculate an overall heat transfer coefficient of a part in which the residue is most likely to be deposited and determine that CIP is completed when the overall heat transfer coefficient becomes equal to or higher than a target value (Patent Literature 5).

SIP is performed by passing a heated steam or heated liquid through the drink filling path. Conventionally, it is determined that SIP is completed when a predetermined time has elapsed since the temperature of a predetermined part in the drink supply piping of the drink filing path reached a predetermined temperature. However, this method involves an unnecessarily long time of SIP and a substantial loss of time and energy. To address this problem, the drink filling apparatus provided with the drink supply piping for feeding the drink into the filling machine through the heat sterilization portion is provided with a plurality of temperature sensors provided on the drink supply piping, F values are calculated from the temperatures detected by the temperature sensors, and it is determined that SIP is completed when the minimum value of the calculated F values reaches a target value (Patent Literatures 6 and 7).

CITATION LIST

Patent Literature

Patent Literature 1: Japanese Patent Laid-Open No. 2007-331801
Patent Literature 2: Japanese Patent Laid-Open No. 2000-153245
Patent Literature 3: Japanese Patent Laid-Open No. 2007-22600
Patent Literature 4: Japanese Patent Laid-Open No. 2019-064722
Patent Literature 5: Japanese Patent Laid-Open No. 2020-70067
Patent Literature 6: International Publication No. 2014/103787
Patent Literature 7: Japanese Patent Laid-Open No. 2015-044593

SUMMARY OF INVENTION

Technical Problem

The aseptic filling machine can ensure the quality of the products manufactured by the aseptic filling machine by performing CIP and SIP of the inside of the drink supply piping with reliability.

As proposed in Patent Literature 4, in the cleaning and sterilizing method for the drink filling apparatus in which CIP for cleaning and SIP for sterilizing the inside of the drink supply piping of the aseptic filling machine are performed, the downtime between CIP and SIP can be eliminated, and CIP and SIP can be performed at the same time or in succession. SIP is performed using the cleaning liquid for CIP circulated in the drink supply piping. SIP and CIP of the inside of the drink supply piping can be performed at the same time or in succession by heating the cleaning liquid used for CIP to a required temperature for SIP from the start of CIP or during CIP. According to this method, the duration of CIP and SIP can be reduced, and the energy consumption can be reduced.

However, in order to reduce the duration of CIP and SIP, the completion of each of CIP and SIP have to be accurately determined.

An object of the present disclosure is to provide a cleaning and sterilizing method for an aseptic filling machine and the aseptic filling machine that can accurately determine the completions of CIP and SIP to reduce the duration of CIP and SIP when SIP and CIP of the inside of content supply piping of the aseptic filling machine are performed at the same time or in succession by heating a cleaning liquid used for CIP to a required temperature for SIP from beginning or during of CIP.

Solution to Problem

A cleaning and sterilizing method for an aseptic filling machine according to the present disclosure is a cleaning and sterilizing method for an aseptic filling machine including content supply piping for feeding a content to an inside of a filler via a heat sterilization portion, wherein CIP (Cleaning In Place) for cleaning an inside of the content supply piping is performed by circulating a cleaning liquid for cleaning the inside of the content supply piping in the content supply piping, SIP (Sterilizing In Place) for sterilizing the inside of the content supply piping is performed by heating the cleaning liquid to a required temperature for sterilization of the inside of the content supply piping from a start of the CIP or during the CIP and circulating the heated cleaning liquid in the content supply piping, temperatures of the cleaning liquid at an inlet and an outlet for the cleaning liquid of heating piping of the heat sterilization portion are measured, temperatures of a heating medium at an inlet and an outlet for the heating medium of the heating piping are measured, an overall heat transfer coefficient of the heating piping is calculated based on the temperatures at the inlet and the outlet for the cleaning liquid of the heating piping and the temperatures at the inlet and the outlet for the heating medium of the heating piping, and it is determined that the CIP is completed when the overall heat transfer coefficient calculated reaches a target value, temperatures are measured by a plurality of temperature sensors provided in the content supply piping, a lowest temperature is selected from the measured temperatures, F values are calculated for the selected lowest temperature, the calculated F values are accumulated, and it is determined that the SIP is completed when an accumulated F value reaches a target value, and the cleaning liquid is discharged after the CIP and the SIP are completed.

In the cleaning and sterilizing method for an aseptic filling machine according to the present disclosure, preferably, an upstream piping portion of the content supply piping that passes through the heat sterilization portion is provided with an upstream feedback path to form an upstream circulation path, and the cleaning liquid is circulated in the upstream circulation path.

An aseptic filling machine according to the present disclosure is an aseptic filling machine including content supply piping for feeding a content to an inside of a filler via a heat sterilization portion, the aseptic filling machine comprising: a cleaning liquid supply apparatus that supplies a cleaning liquid for cleaning an inside of the content supply piping to the inside of the content supply piping, a circulation path for circulating the cleaning liquid supplied in the content supply piping, the circulation path being configured so that SIP (Sterilizing In Place) for sterilizing the inside of the content supply piping is performed by heating the cleaning liquid to a required temperature for sterilization of the inside of the content supply piping from a start of CIP (Cleaning In Place) or during the CIP of the inside of the content supply piping, which is performed using the cleaning liquid being circulated, and circulating the heated cleaning liquid in the content supply piping, temperature sensors that measure temperatures of the cleaning liquid at an inlet and an outlet for the cleaning liquid of heating piping of the heat sterilization portion, temperature sensors that measure temperatures of a heating medium at an inlet and an outlet for the heating medium of the heating piping, a plurality of temperature sensors in the content supply piping, a controller, the controller being configured to calculate an overall heat transfer coefficient of the heating piping based on the temperatures at the inlet and the outlet for the cleaning liquid of the heating piping and the measured temperatures at the inlet and the outlet for the heating medium of the heating piping, determine that the CIP is completed when the overall heat transfer coefficient calculated reaches a target value, select a lowest temperature from measured temperatures by the plurality of temperature sensors, calculate F values for the selected lowest temperature, accumulate the calculated F values, determine that the SIP is completed when an accumulated F value reaches a target value, and indicate to discharge the cleaning liquid after the CIP and the SIP are completed.

In the aseptic filling machine according to the present disclosure, preferably, an upstream piping portion of the content supply piping that passes through the heat sterilization portion is provided with an upstream feedback path to form an upstream circulation path, and the upstream circulation path is configured so that the cleaning liquid is circulated in the upstream circulation path.

Advantageous Effects of Invention

According to the present disclosure, concerning CIP and SIP of the content supply piping of the aseptic filling machine, when CIP for cleaning the inside of the content supply piping and SIP for sterilizing the inside of the content supply piping are performed at the same time or in succession by heating the cleaning liquid used for CIP to a required temperature for sterilization of the inside of the content supply piping from the start of CIP or during CIP, the overall heat transfer coefficient of the heating piping of the heat sterilization portion is calculated, F values calculated from the lowest temperature measured by the temperature sensor in the content supply piping are accumulated, and it is determined that CIP is completed when the overall heat transfer coefficient reaches a target value, and it is determined that SIP is completed when the accumulated F value reaches a target value. As a result, the duration of CIP and SIP can be reduced, the subsequent filling operation with a content can be started earlier, the preparation time between manufacturing processes for changing contents can be reduced, and the production efficiency can be improved. In addition, since the duration of CIP and SIP is reduced, the energy consumption is reduced, and the emission of $CO_2$ is reduced.

In the cleaning and sterilizing method for the aseptic filling machine according to the present disclosure, the lowest temperature is selected from the temperatures measured by a plurality of temperature sensors provided in the content supply piping, F values are calculated from the selected temperature, the calculated F values are accumulated, and it is determined that the SIP is completed when the accumulated F value reaches a target value. According to this method, the number of calculations of F values can be reduced, and therefore, the cost of the calculation apparatus can be substantially reduced compared with the case where F values are calculated for all the measured temperatures.

DESCRIPTION OF EMBODIMENT

In the following, an embodiment of the present disclosure will be described with reference to the drawings.

Figure 1:
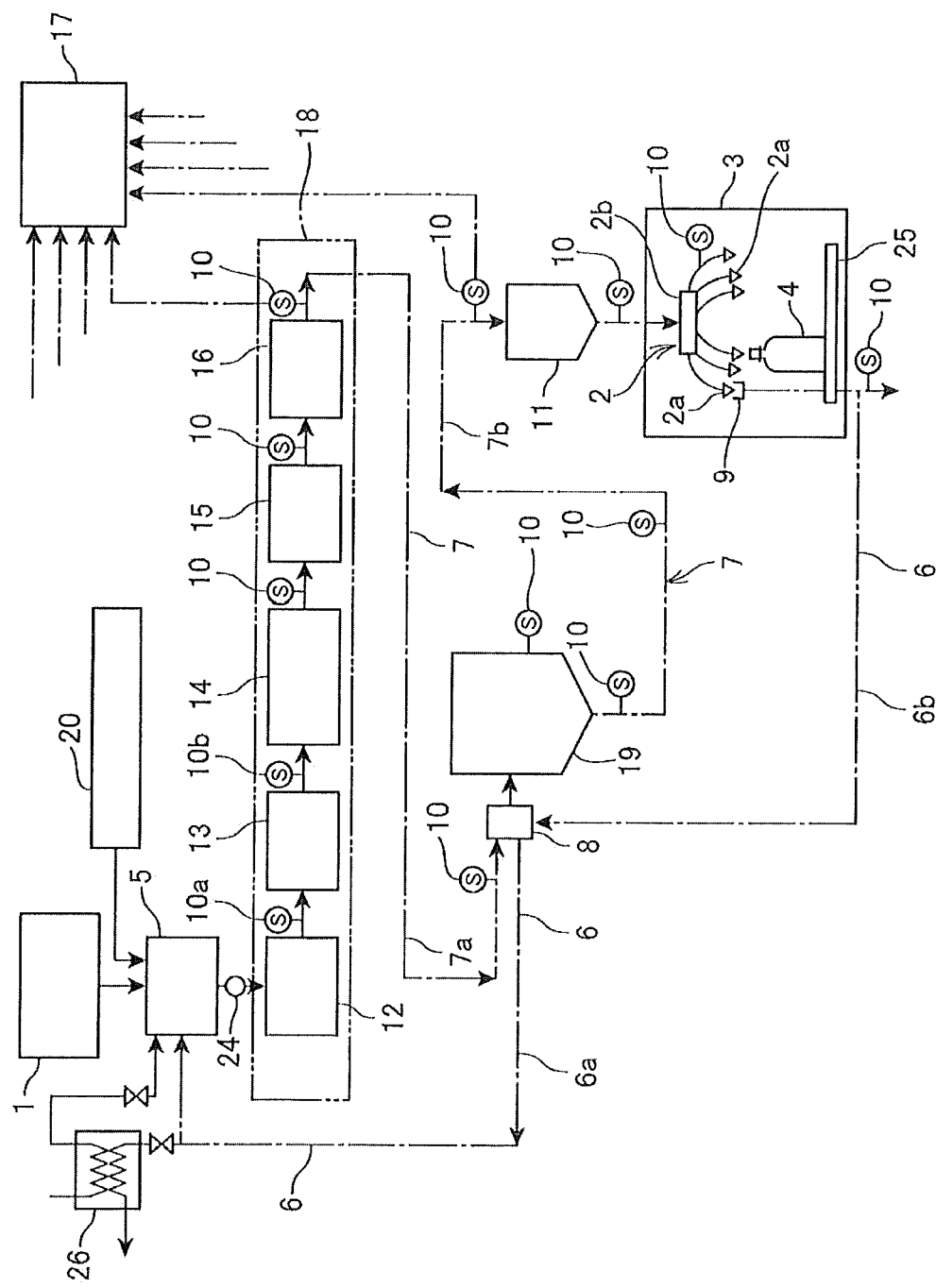
FIG. 1 is a block diagram showing an aseptic filling machine according to an embodiment of the present disclosure.

As shown in FIG. 1, an aseptic filling machine includes a content preparation apparatus 1 and a filler 2 that fills a container 4 such as a bottle with a content. The preparation apparatus 1 and a filling nozzle 2a in the filler 2 are connected by content supply piping 7. A filling portion, which includes the filler 2, is shielded by a filling portion chamber 3.

The preparation apparatus 1 prepares a content such as coffee with milk, black coffee, a green tea drink, tea, tea with milk or a fruit juice drink according to a desired formula, and detailed description thereof will be omitted since the preparation apparatus 1 is a well-known apparatus.

The aseptic filling machine is provided with a conveyor path for conveying the container 4 to the filler 2 and ejecting the container 4 filled with a content by the filler 2. The conveyor path is typically formed by a large number of wheels and grippers or the like arranged around the wheels for holding the container 4.

The filler 2 is an apparatus that includes a large number of filling nozzles 2a arranged around a wheel (not shown) that rotates at high speed in a horizontal plane, and fills containers 4 gripped by grippers and traveling below the filling nozzles 2a in synchronization with the circumferential speed of the wheel with a fixed amount of content from the filling nozzles 2a rotating with the wheel. The filler 2 is also a well-known apparatus, and detailed description thereof will be omitted.

In the filling portion chamber 3 that shields the filling portion provided with the filler 2 of the aseptic filling machine, COP (Cleaning Out of Place) for cleaning the inside of the filling portion chamber 3 and SOP (Sterilizing Out of Place) for sterilizing the inside of the filling portion chamber 3 are performed before an aseptic filling by the aseptic filling machine. Aseptic water is required for COP, SOP, cleaning of a cap after the sterilization and cleaning of an outer surface of a mouth portion of the container after the filling of the container with a content, and therefore, the aseptic filling machine may be provided with an aseptic water production apparatus (not shown).

Viewed from the upstream to the downstream of the flow of the content along the pipe line from the preparation apparatus 1 to the filler 2, the content supply piping 7 of the aseptic filling machine includes a balance tank 5, a heat sterilization portion 18, a manifold valve 8, an aseptic surge tank 19 and a filler tank 11. The aseptic filling machine also includes a cleaning liquid supply apparatus 20 that supplies a cleaning liquid to the balance tank 5 and a controller 17 that controls the operation of the aseptic filling machine.

When the content is carbonated to produce a carbonated drink, the content supply piping 7 of the aseptic filling machine includes a cooling apparatus (not shown), a carbonating apparatus and a carbonated drink surge tank. The cooling apparatus, the carbonating apparatus and the carbonated drink surge tank are provided in the listed order from upstream to downstream between the aseptic surge tank 19 and the filler tank 11, and a carbonated drink manifold valve is provided for flowing the carbonated drink through the content supply piping.

The heat sterilization portion 18 includes therein a first-stage heating portion 12, a second-stage heating portion 13, a holding tube 14, a first-stage cooling portion 15, and a second-stage cooling portion 16, for example. The content, cleaning liquid or the like supplied from the balance tank 5 is gradually heated while being fed from the first-stage heating portion 12 to the second-stage heating portion 13, kept at a predetermined sterilization temperature for a predetermined time in the holding tube 14, and then fed to the first-stage cooling portion 15 and the second-stage cooling portion 16 and gradually cooled. The number of stages of the heating portions and the cooling portions is increased or decreased as required. The heat sterilization portion 18 may be provided with a homogenizer before or after the holding tube 14.

The balance tank 5, the manifold valve 8, the aseptic surge tank 19 and the filler tank 11 are well-known apparatus, and detailed description thereof will be omitted.

The content is prepared by the preparation apparatus 1, fed from the balance tank 5 to the heat sterilization portion 18, and is subjected to a heat sterilization process in the heat sterilization portion 18. The content subjected to the heat sterilization process in the heat sterilization portion 18 is stored in the aseptic surge tank 19 and then fed to the filler tank 11. The content in the filler tank 11 is supplied to the filler 2, and the container 4 is filled with the content through the filling nozzle 2a in an aseptic condition. The container 4 filled with the content is sealed and then ejected to the outside of the aseptic filling machine.

The content supplied from the balance tank 5 is fed to the first-stage heating portion 12 and the second-stage heating portion 13 of the heat sterilization portion 18, and the content at room temperature (20° C.), for example, is heated to 140° C., for example, in the first-stage heating portion 12 and the second-stage heating portion 13. The heat sterilization process is performed on the content while the content is being heated from room temperature to 140° C. in this way.

The content heated in the first-stage heating portion 12 and the second-stage heating portion 13 is kept at the temperature or heated to a target temperature such as 140° C. by a heating mechanism (not shown) in the holding tube 14.

The content from the holding tube 14 is cooled in the first-stage cooling portion 15 from 140° C. to 80° C., for example. The content cooled in the first-stage cooling portion 15 is further cooled in the second-stage cooling portion 16 from 80° C. to 30° C., for example. The cooled content is fed to the aseptic surge tank 19 via the manifold valve 8.

The content fed to and stored in the aseptic surge tank 19 is fed to and stored in the filler tank 11 and fed to the filler 2, and the sterilized container 4 is filled with a fixed amount of the content from the filling nozzle 2a in the aseptic atmosphere in the filling portion chamber 3. The container 4 filled with the content is sealed with a sterilized lid member and then ejected from the aseptic filling machine.

When contents are changed or the operation of the aseptic filling machine is stopped for a certain time after the aseptic filling operation with the content ends, CIP and SIP of the inside of the content supply piping 7 are performed. The part in which the residue of the content is most likely to be deposited in the content filling operation is the second-stage heating portion. The second-stage heating portion is a part in which the temperature of the content is rapidly raised, so that the residue is particularly likely to be deposited in the second-stage heating portion because of the heat denaturation of protein, and this is remarkable when the content contains milk. The higher the temperature or the higher the flowrate of the fed liquid, the larger the amount of minerals derived from the ingredients of the product remains. The residue of the content used in the previous filling is removed by CIP.

CIP of the inside of the content supply piping 7 is performed by circulating a cleaning liquid supplied from the cleaning liquid supply apparatus 20 to the balance tank 5 in the content supply piping 7. To this end, as shown in FIG. 1, the content supply piping 7 is provided with a feedback path 6 to form a circulation path. The feedback path 6 for an upstream piping portion 7a extending from the balance tank 5 to the manifold valve 8 via the heat sterilization portion 18 may be provided with an upstream feedback path 6a to form an upstream circulation path.

The cleaning liquid may not be circulated in the upstream circulation path but may be flowed from the manifold valve 8 to the filler 2 via the filler tank 11, and a filler manifold 2b of the filler 2 may distribute the cleaning liquid to the filling nozzles 2a. The cleaning liquid flowing out from the filling nozzles 2a is received by cups 9 connected to the tip ends of the filling nozzles 2a, and the cleaning liquid flowing out of the large number of filling nozzles 2a is collected by a circulation manifold 25 and fed back to the manifold valve 8 through a downstream feedback path 6b. The cleaning liquid circulates in the content supply piping 7 by passing through the upstream feedback path 6a from the manifold valve 8.

Cups 9, each of which can be connected to and disconnected from the opening of a filling nozzle 2a, are arranged at openings of the filling nozzles 2a of the filler 2. When performing CIP or SIP, an actuator (not shown) couples each cup 9, which will form the starting end of the downstream feedback path 6b, to an opening portion at the tip end of a filling nozzle 2a of the filler 2, thereby connecting the cup 9 to the opening of the filling nozzle 2a.

Figure 2:
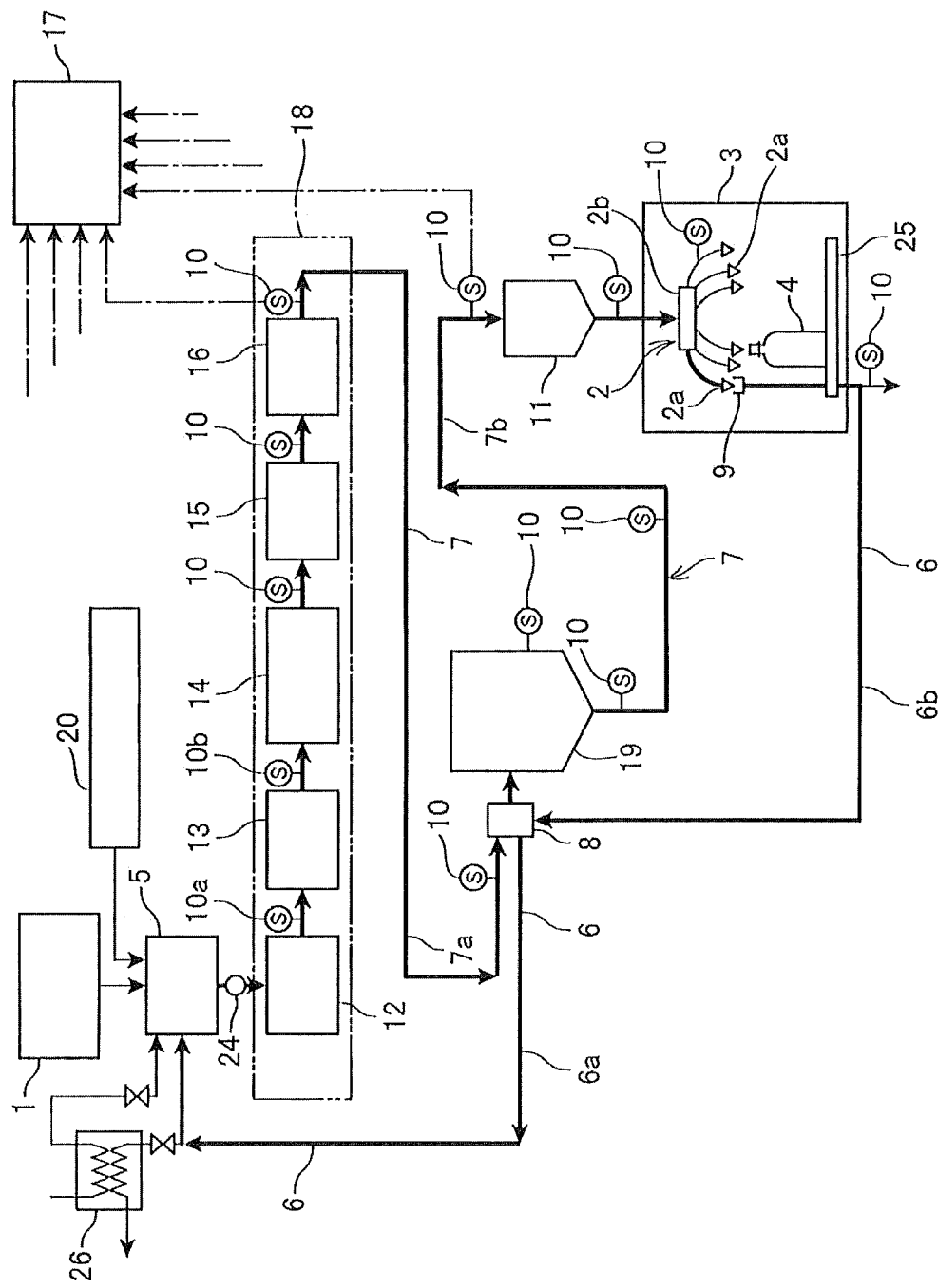
FIG. 2 is a block diagram showing the aseptic filling machine according to the embodiment of the present disclosure in a state where CIP and/or SIP are performed on content supply piping from a heat sterilization portion to a filler.

As shown by the thick line in FIG. 2, the cleaning liquid supplied from the cleaning liquid supply apparatus 20 to the balance tank 5 circulates in the content supply piping 7 from the balance tank 5 by being heated by the heat sterilization portion 18, passing through the manifold valve 8, the aseptic surge tank 19 and the filler tank 11 to reach the filler 2, flowing from the filler manifold 2b to the filling nozzles 2a, being received by the cups 9 from the filling nozzles 2a and collected by the circulation manifold 25, passing through the downstream feedback path 6b and passing through the upstream feedback path 6a via the manifold valve 8 back to the balance tank 5.

Figure 3:
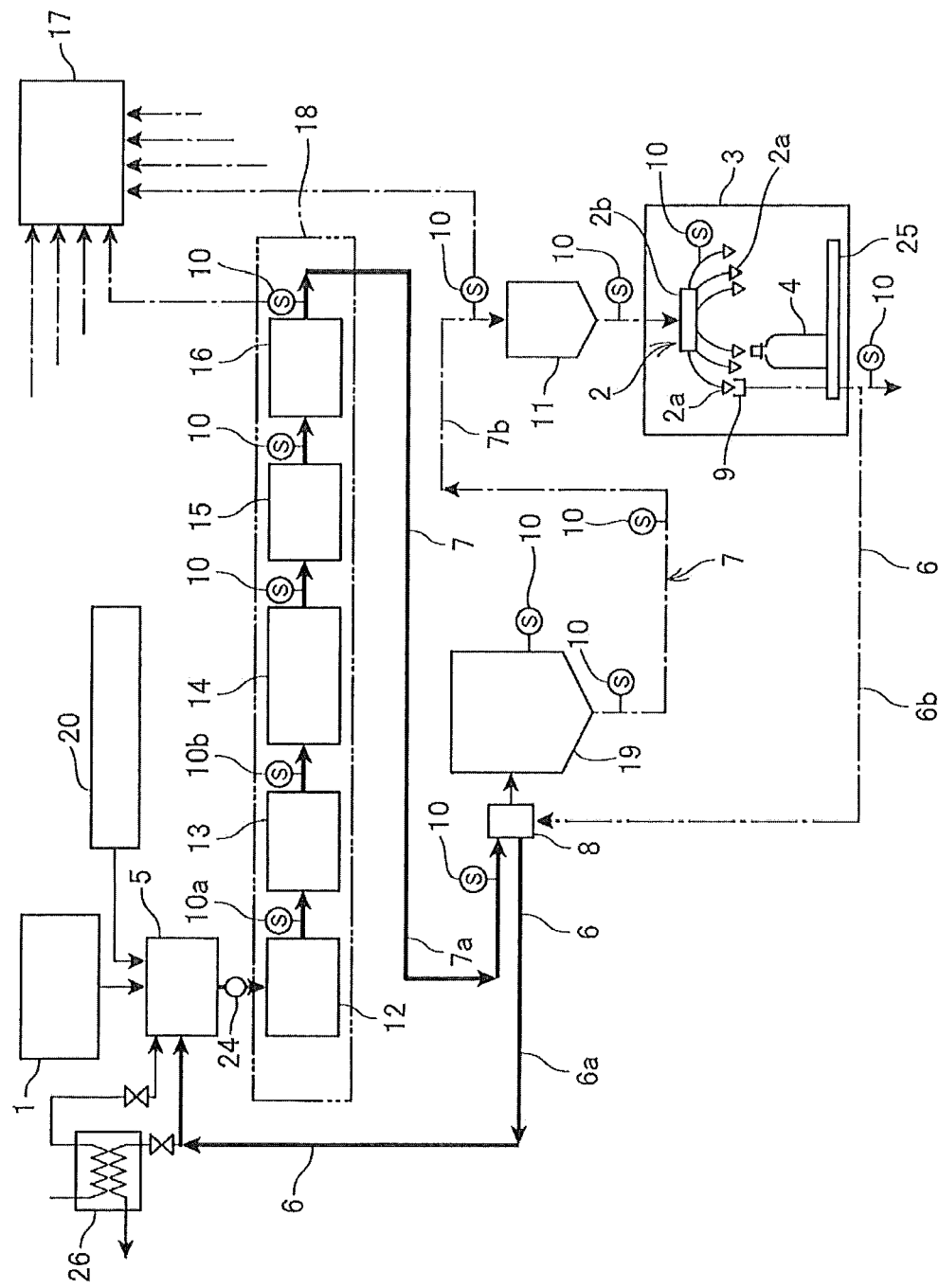
FIG. 3 is a block diagram showing the aseptic filling machine according to the embodiment of the present disclosure in a state where CIP and/or SIP are performed on an upstream piping portion of the content supply piping including the heat sterilization portion.

As shown by the thick line in FIG. 3, the cleaning liquid supplied from the cleaning liquid supply apparatus 20 to the balance tank 5 may be circulated in the upstream circulation path from the balance tank 5 by being heated by the heat sterilization portion 18, reaching the manifold valve 8 and passing through the upstream feedback path 6a back to the balance tank 5.

The cleaning liquid is an alkaline cleaning liquid containing water and an alkaline chemical agent as an additive such as caustic soda (sodium hydroxide), potassium hydroxide, sodium carbonate, sodium silicate, sodium phosphate, sodium hypochlorite, surfactant and a chelating agent (sequestering agent) such as sodium gluconate and ethylenediamine tetraacetic acid (EDTA), or an acidic cleaning liquid containing water and a nitric acid-based or phosphoric acid-based acidic chemical agent as an additive. The water can be any water containing no foreign matters, such as ion exchanged water, distilled water or tap water.

The alkaline cleaning liquid may contain lithium carbonate, ammonium carbonate, magnesium carbonate, calcium carbonate, propylene carbonate or a mixture thereof, although the alkaline cleaning liquid is not limited to these. The alkaline cleaning liquid may also contain a bicarbonate such as sodium bicarbonate, potassium bicarbonate, lithium bicarbonate, ammonium bicarbonate, magnesium bicarbonate or calcium bicarbonate, a sesquicarbonate such as a sodium sesquicarbonate, potassium sesquicarbonate or lithium sesquicarbonate, or a mixture thereof.

The acidic cleaning liquid may contain not only the nitric acid or phosphoric acid described above but also hydrochloric acid, sulfuric acid, acetic acid, citric acid, lactic acid, formic acid, glycolic acid, methanesulfonic acid, sulfamic acid, or a mixture thereof, although the acidic cleaning liquid is not limited to these.

The cleaning liquid may contain various bleaching agent such as hypochlorite, hydrogen peroxide, peracetic acid, peroctanoic acid, persulfate, perborate, hydrosulfite or thiourea dioxide, or percarbonate, for example. Furthermore, the cleaning liquid may contain a water softener such as aluminosilicate or polycarboxylate, or may contain an antiredeposition agent such as sodium phosphate, sodium polyacrylate or sodium carboxylate. Furthermore, an enzyme, a solvent, fatty acid, a foam modifier or an active oxygen source may be added to the cleaning liquid, for example.

As cleaning liquids used in CIP, an alkaline cleaning liquid can be flowed first, and then an acidic cleaning liquid can be flowed, although the order of flowing cleaning liquids is not limited to this order. For example, an acidic cleaning liquid may be flowed first, and then an alkaline cleaning liquid may be flowed, or an acidic cleaning liquid and an alkaline cleaning liquid may be alternately flowed multiple times. Alternatively, only one of an acidic cleaning liquid and an alkaline cleaning liquid may be flowed for CIP.

A fixed amount of cleaning liquid is constantly or intermittently supplied from the cleaning liquid supply apparatus 20, and the cleaning liquid circulates and removes any residue of the previous content deposited on the inside of the content supply piping 7. To activate the cleaning liquid, the temperature of the cleaning liquid may be raised to a predetermined temperature by the heat sterilization portion 18. The predetermined temperature is 60° C. to 150° C., and raising the temperature can improve the cleaning effect and produce the sterilizing effect. The cleaning liquid being circulated may be discharged to the outside of the machine as required.

SIP is performed after CIP. A liquid feeding pump used for CIP is not stopped to keep the cleaning liquid used for CIP circulating in the content supply piping 7, and the cleaning liquid is heated to a required temperature for SIP by the heat sterilization portion 18. SIP is performed in succession to CIP by circulating the cleaning liquid heated to a higher temperature in the content supply piping 7. In this process, since the liquid feeding pump is not stopped, the set temperature of the heat sterilization portion 18 raised in CIP is not lowered but raised to a temperature for SIP, and therefore, the temperature of the inside of the content supply piping 7 including the heat sterilization portion 18 does not decrease in the transition from CIP to SIP.

Figure 5:
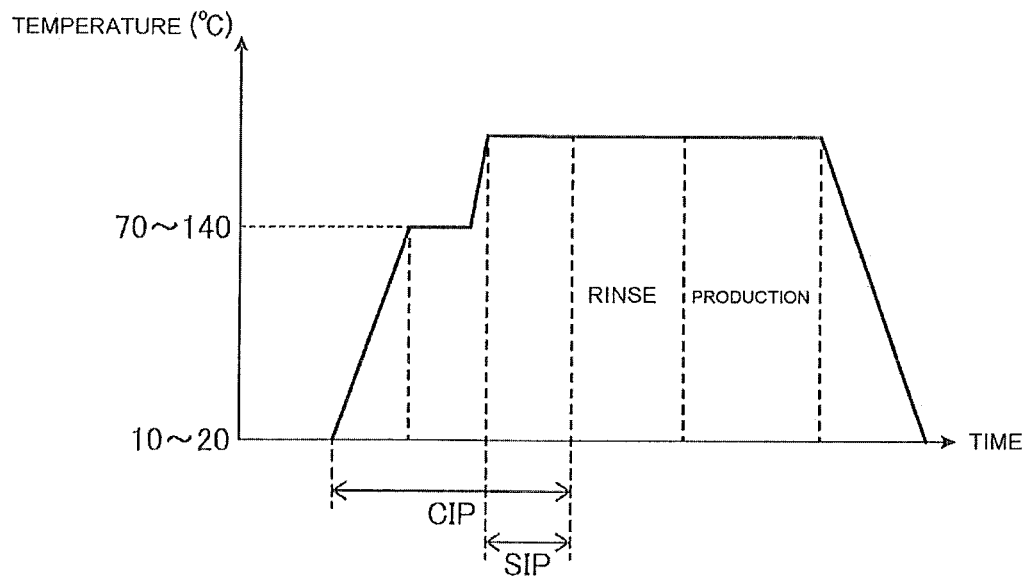
FIG. 5 is a graph showing a variation of the temperature of a second-stage heating portion of the heat sterilization portion with time in another cleaning and sterilizing method for the aseptic filling machine according to the embodiment of the present disclosure.

FIG. 5 shows the temperature of the second-stage heating portion 13 of the heat sterilization portion 18 when CIP and SIP are performed in succession. The cleaning liquid is supplied from the cleaning liquid supply apparatus 20 to the heat sterilization portion 18 via the balance tank 5 and heated to a temperature for CIP. The cleaning liquid heated to the temperature for CIP is circulated in the circulation path for a predetermined time. After circulating for the predetermined time, the cleaning liquid is heated to a required temperature for SIP and circulates for a predetermined time until SIP is completed. During SIP, the cleaning liquid is circulating, so that CIP is also performed. After SIP is completed, water is supplied to the heat sterilization portion 18 to rinse the cleaning liquid. The rinsed cleaning liquid is received by the cups through the filling nozzles 2a, collected by the circulation manifold 25 and then discharged. Alternatively, the cleaning liquid may pass through the downstream feedback path 6b and the upstream feedback path 6a and be discharged immediately before the balance tank 5. After the cleaning liquid is rinsed off, products can be immediately manufactured by filling containers with the content without changing the set temperature of the heat sterilization portion 18.

The cleaning liquid used for CIP may be heated to the required temperature for SIP by the heat sterilization portion 18 while being kept circulating after the end of CIP. Alternatively, the cleaning liquid may be heated to the required temperature for SIP at the start of CIP, and CIP and SIP may be performed at the same time.

Figure 4A:
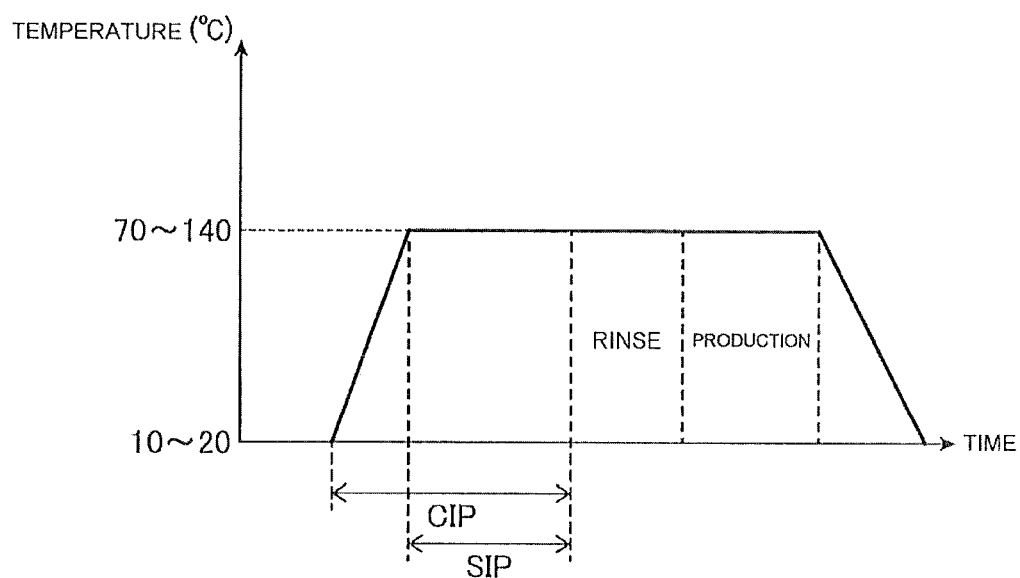
FIG. 4A is a graph showing a variation of the temperature of a second-stage heating portion of the heat sterilization portion with time in a cleaning and sterilizing method for the aseptic filling machine according to the embodiment of the present disclosure.

FIG. 4A shows the temperature of the second-stage heating portion 13 of the heat sterilization portion 18 when CIP and SIP are performed at the same time. The cleaning liquid is supplied from the cleaning liquid supply apparatus 20 to the heat sterilization portion 18 via the balance tank 5 and heated to a required temperature for SIP. The cleaning liquid is circulated for a predetermined time until CIP and SIP are completed. After SIP is completed, water is supplied to the heat sterilization portion 18 to rinse the cleaning liquid. The rinsed cleaning liquid is received by the cups 9 through the filling nozzles 2a and discharged through the circulation manifold 25. Alternatively, the cleaning liquid may pass through the downstream feedback path 6b and the upstream feedback path 6a and be discharged immediately before the balance tank 5. After the cleaning liquid is rinsed off, products can be immediately manufactured by filling containers with the content without changing the set temperature of the heat sterilization portion 18.

Figure 4B:
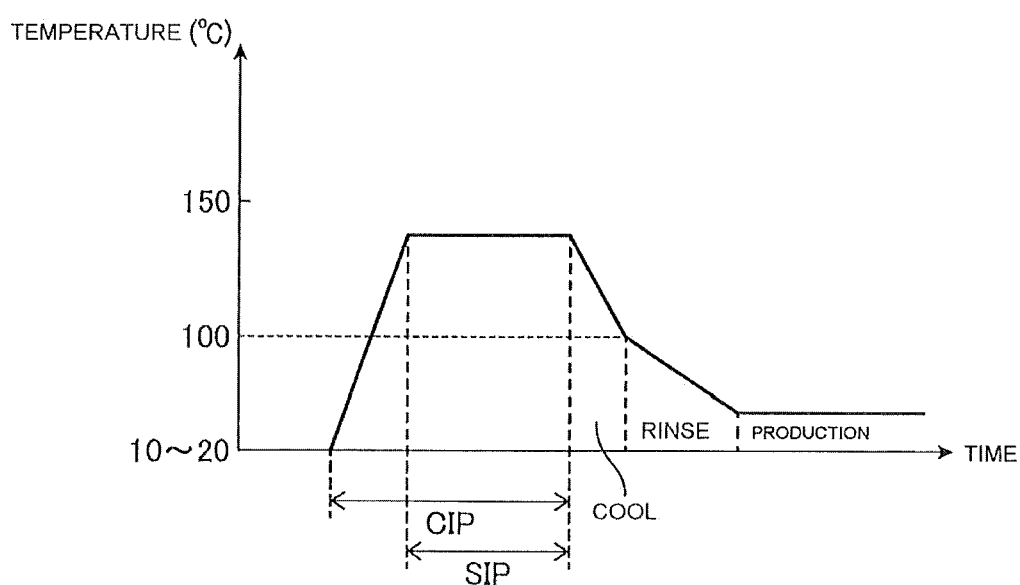
FIG. 4B is a graph showing a variation of the temperature of a second-stage cooling portion of the heat sterilization portion with time in the cleaning and sterilizing method for the aseptic filling machine according to the embodiment of the present disclosure.

FIG. 4B shows the temperature of the second-stage cooling portion 16 of the heat sterilization portion 18 when CIP and SIP are performed at the same time. The cleaning liquid is supplied from the cleaning liquid supply apparatus 20 to the heat sterilization portion 18 via the balance tank 5 and heated to a required temperature for SIP. The cleaning liquid is circulated for a predetermined time until CIP and SIP are completed. After SIP is completed, the first-stage and/or second-stage cooling portions (15 and/or 16) are activated, and the cleaning liquid is circulated until the temperature of the second-stage cooling portion 16 becomes equal to or lower than 100° C. When the temperature of the cleaning liquid passing through the outlet of the second-stage cooling portion becomes equal to or lower than 100° C., a discharge valve, which is provided on the circulation path for discharging the cleaning liquid, is opened to switch the circulation path to an open path, water is supplied to the heat sterilization portion 18, and the heat sterilization portion 18 heats and sterilizes the supplied water to make the water aseptic. The cleaning liquid is rinsed off by the aseptic water.

When rinsing the cleaning liquid, the cleaning liquid at the high temperature to be discharged without being cooled and the supplied rinse water at room temperature may be passed through a heat exchanger 26 to raise the temperature of the rinse water before the rinse water is supplied to the heat sterilization portion. This can reduce the thermal energy consumption. The aseptic rinse water may be introduced from another aseptic water production facility.

As shown in FIG. 1, temperature sensors 10, 10a and 10b are arranged at locations in the heat sterilization portion 18. A location where the temperature sensor 10a is arranged is the inlet of the second-stage heating portion 13, and a location where the temperature sensor 10b is arranged is the outlet of the second-stage heating portion 13. Information on the temperatures measured by these temperature sensors 10, 10a and 10b is transmitted to the controller 17.

Figure 6:
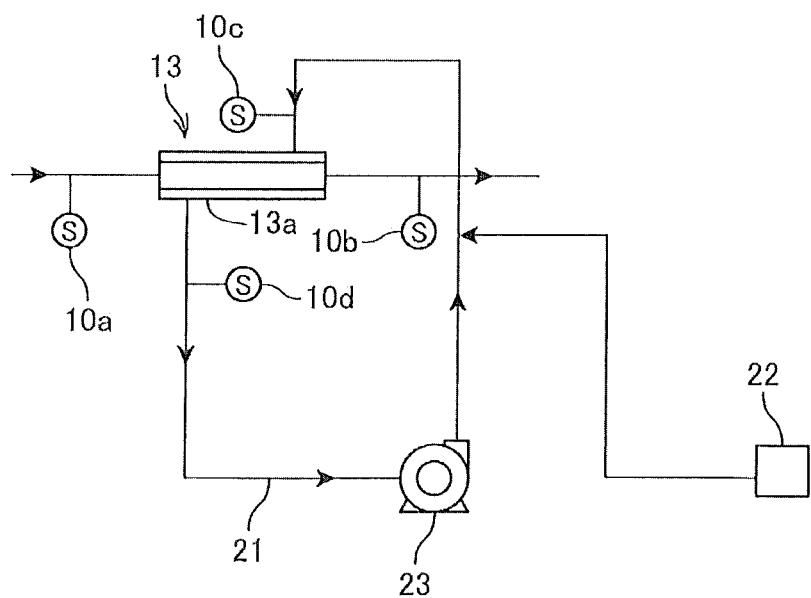
FIG. 6 is a diagram showing a heating medium line connected to the second-stage heating portion of the aseptic filling machine according to the embodiment of the present disclosure.

As shown in FIG. 6, in order to heat the second-stage heating portion 13 located at the downstream end of the heating portions 12 and 13, a heating medium line 21 for supplying a heating medium is connected to the second-stage heating portion 13.

The heating medium line 21 is provided with a heated steam supply portion 22 that supplies heated steam to the heating medium line 21, and the heating medium flowing in the heating medium line 21 is heated to a high temperature by the heated steam supplied from the heated steam supply portion 22. The heating medium may be heated by an electric heater. The heating medium line 21 is further provided with a pressure pump 23. A suitable heating medium is water. In addition to water, oil can also be used. However, since oil cannot be heated by heated steam, a heating apparatus need to be provided.

The heating medium line 21 is connected to heating piping 13a of the second-stage heating portion, and the heating medium flows in the heating piping 13a in the opposite direction to the direction in which the content flows in the content supply piping 7. The heating medium may flow in the same direction as the content flowing in the content supply piping 7 in parallel with the content. A temperature sensor 10c is provided at the inlet of the heating piping 13a, and a temperature sensor 10d is provided at the outlet of the heating piping 13a. In addition, a flowmeter 24 that measures the flowrate of the content flowing in the content supply piping 7 is provided between the balance tank 5 and the heat sterilization portion 18.

As shown in FIG. 6, the heating medium flowing in the heating medium line 21 is supplied to the heating piping 13a to heat the content flowing in the second-stage heating portion 13. Although the temperature of the heating medium that heats the content in the second-stage heating portion 13 is lowered until the heating medium reaches the outlet of the heating piping 13a, the heating medium is heated by the heated steam supplied from the heated steam supply portion 22, and the heating medium heated is supplied to the heating piping 13a and circulates.

The second-stage heating portion 13 of the heat sterilization portion 18 is a part that heats and sterilizes the content at high temperature, and soil such as burnt deposit is likely to occur on the inner surface of the heating piping 13a. In this embodiment, the overall heat transfer coefficient of the heating piping 13a of the second-stage heating portion 13 that is most likely to be soiled is calculated to efficiently perform CIP of the inside of the heat sterilization portion 18. The overall heat transfer coefficient can be calculated for the other heating portions and cooling portions of the heat sterilization portion 18. The overall heat transfer coefficient should be calculated for all the heating portions and cooling portions, and CIP should be completed when all the overall heat transfer coefficients reach a target value. However, the part where the amount of residue of the content is the largest is the heating portion at the downstream end, and it can be determined that CIP is completed when the overall heat transfer coefficient of the heating portion at the downstream end reaches a target value.

Figure 7:
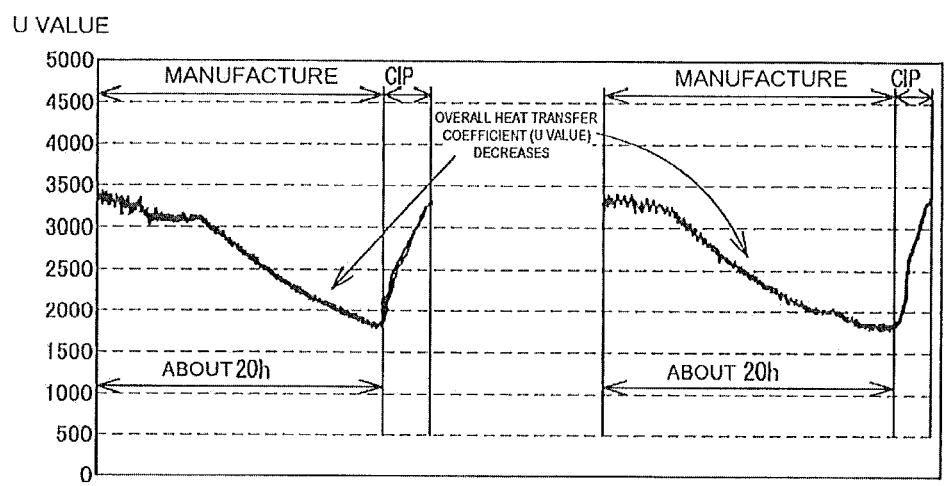
FIG. 7 is a diagram showing variations of an overall heat transfer coefficient (U value) of the second-stage heating portion of the aseptic filling machine according to the embodiment of the present disclosure during manufacture and during CIP.

FIG. 7 shows temporal variations of the overall heat transfer coefficient (U value) with production time. Higher overall heat transfer coefficient (U value) means that heat is more likely to be transferred. The overall heat transfer coefficient of the heating piping 13a gradually decreases as products are manufactured because of deposits of the content such as burnt deposit formed on the inside of the heating piping 13a in the course of the sterilization of the content. The overall heat transfer coefficient having decreased in the course of manufacture is raised by performing CIP, and the overall heat transfer coefficient before the start of manufacture is recovered. That is, a basis for completion of CIP is that the overall heat transfer coefficient of the heating piping 13a recovers to the overall heat transfer coefficient in the state where no residue of the content is deposited in the heating piping 13a. A target value of the decreased overall heat transfer coefficient is determined, and it is determined that CIP is completed when the overall heat transfer coefficient of the heating piping 13a reaches the target value as a result of CIP. In this way, no time is wasted in CIP, and CIP can be efficiently performed.

The controller 17 stores various kinds of data, calculates the overall heat transfer coefficient from the measured temperatures transmitted from the heating piping 13a of the second-stage heating portion 13, determines whether or not the calculated overall heat transfer coefficient reaches the target value, determines that CIP is completed when the overall heat transfer coefficient reaches the target value, and completes CIP of the inside of the content supply piping 7. This determination of completion is made for the second-stage heating portion 13 of the heat sterilization portion 18. Since the second-stage heating portion of the heat sterilization portion 18 is most heavily soiled, the determination of completion of CIP of the second-stage heating portion 13 of the heat sterilization portion 18 may be considered as the determination of completion of CIP of the inside of the content supply piping 7.

To calculate the overall heat transfer coefficient, as shown in FIG. 6, the temperature sensor 10a is provided at the inlet for the cleaning liquid of the heating piping 13a of the second-stage heating portion 13 of the heat sterilization portion 18, the temperature sensor 10b is provided at the outlet for the cleaning liquid, the temperature sensor 10c is provided at the inlet for the heating medium of the heating piping 13a, and the temperature sensor 10d is provided at the outlet for the heating medium of the heating piping 13a. These temperature sensors measure temperature, the temperature from the temperature sensor 10a is denoted as T1, the temperature from the temperature sensor 10b is denoted as T2, the temperature from the temperature sensor 10c is denoted as T3, and the temperature from the temperature sensor 10d is denoted as T4.

The measured temperatures T1, T2, T3 and T4 are transmitted to the controller 17, and the controller 17 calculates the overall heat transfer coefficient. The overall heat transfer coefficient is determined as follows.

First, a logarithmic mean temperature difference $\Delta T$ is determined. The logarithmic mean temperature difference $\Delta T$ is determined as follows.

[Expression 1]

$$\Delta T = \left| \frac{((T4-T1)-(T3-T2))}{\ln((T4-T1)/(T3-T2))} \right|$$ (Formula 1)

A heat quantity Q in the second-stage heating portion 13 is then determined from the temperatures T1 and T2 and a flowrate R(L/h). Provided that the specific heat is 1 (kcal/kg*°C.), and the specific weight is 1 (kg/L), $$Q = 1 \times 1 \times R \times (T2-T1)$$ (Formula 2)

The flowrate R is measured by the flowmeter 24 and is transmitted to the controller 17.

A heat transfer area A(m$^2$) of the heating piping 13a of the second-stage heating portion 13 is determined in advance.

On this condition, the controller 17 calculates the overall heat transfer coefficient (U value) of the second-stage heating portion 13 according to $$U = Q/(A \times \Delta T)$$ (Formula 3).

As described above, according to this embodiment, the overall heat transfer coefficient of the second-stage heating portion 13 is calculated during CIP, and when the overall heat transfer coefficient reaches a target value, it is determined that CIP is completed and the process can proceed to the next step. Therefore, CIP need not be performed for an unnecessarily long time and can be efficiently performed.

The controller 17 determines that CIP is completed when the calculated overall heat transfer coefficient reaches the target value determined in advance. In CIP in FIG. 4A or 5, if the overall heat transfer coefficient has not reached the target value when SIP is completed, CIP continues.

SIP for sterilizing the inside of the content supply piping 7 is performed by circulating the cleaning liquid for CIP that cleans the inside of the content supply piping 7 in the content supply piping 7 to perform CIP of the inside of the content supply piping 7, heating the cleaning liquid to a required temperature for sterilization of the inside of the content supply piping 7 from the start of CIP or during CIP, and circulating the heated cleaning liquid in the content supply piping 7.

As shown in FIG. 1, the temperature sensors 10 are arranged at locations on the content supply piping 7 including locations where the temperature is less likely to rise in SIP. The locations where the temperature sensors 10 are arranged include locations between components in the heat sterilization portion 18, the location of the outlet of the second-stage cooling portion 16, the location before the manifold valve 8, a location in the aseptic surge tank 19, a location near the outlet of the aseptic surge tank 19, the location of a bent part of the pipe line between the aseptic surge tank 19 and the filling nozzles 2a, locations near the inlet and outlet of the filler tank 11, a location between the filler manifold 2b and the filling nozzles 2a in the filler 2 and a location in a filling nozzle 2a on the pipe line between the first-stage heating portion 12 in the heat sterilization portion 18 and the manifold valve 8, for example. The temperature sensors 10 are arranged at these locations on the pipe line. Information on the temperatures measured by the temperature sensors 10 is transmitted to the controller 17.

When the cleaning liquid is flowing in the content supply piping 7, a plurality of temperatures measured at predetermined time intervals by the temperature sensors 10 arranged at locations in the content supply piping 7 is transmitted to the controller 17 at regular time intervals. The controller 17 selects the lowest temperature from the temperatures measured at a time and calculates the F value. Since the controller 17 selects the lowest temperature, the selected temperature is not always the temperature from the same temperature sensor 10. The temperature sensors 10 measure temperature and transmit the temperature to the controller 17 at predetermined time intervals, and the location where the temperature is the lowest of the measured temperatures is not always the same location.

When the selected lowest temperature of the temperatures at the locations raised by heating by the cleaning liquid reaches 121.1° C., the controller 17 starts calculating the F value based on the lowest temperature. The calculation formula is as follows. Although the Z value in the calculation formula is 10° C., which is a typical value for heat resistant spores, the Z value may be changed in a range from 3° C. to 30° C. as required, based on the resistance of the target fungus to the heat of the cleaning liquid.

$$F=\int_{t_0}^{t_1} 10^{(T-121.1)/10} dt \qquad \text{[Expression 2]}$$

where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

In the case of a highly acidic drink having a pH lower than 4.0, the reference temperature may be 65° C. rather than 121.1° C. When pH is equal to or higher than 4.0 and lower than 4.6, the reference temperature may be equal to or higher than 85° C. When the lowest temperature is lower than the reference temperature during accumulation of the F values, the accumulation of the F values may be stopped and the accumulation may be resumed after the lowest temperature becomes higher than the reference temperature. Preferably, however, SIP is stopped, the accumulation of the F values is reset, and SIP is performed again.

The controller 17 accumulates the F values for the lowest temperature calculated according to the formula described above, and when the accumulated F values reaches the target value, the controller 17 indicates to complete the sterilization step, which is SIP of the inside of the content supply piping 7. According to the indication, the circulation of the cleaning liquid is stopped, and cooling water is supplied to the first-stage cooling portion 15 and the second-stage cooling portion 16 to cool the cleaning liquid. After rinsing is performed to rinse the cleaning liquid off with aseptic water, the aseptic filling machine waits for the next manufacturing process while the aseptic water is continuously circulated.

The required temperature for SIP is typically equal to or higher than 121.1° C. Depending on the content with which the containers are filled by the aseptic filling machine, however, the temperature need not be equal to or higher than 121.1° C. For example, in the case of a highly acidic drink having a pH lower than 4.0, the temperature may be equal to or higher than 65° C. When pH is equal to or higher than 4.0 and lower than 4.6, the temperature may be equal to or higher than 85° C.

In FIG. 3, CIP of the inside of the upstream piping portion 7a may be performed by circulating the cleaning liquid in the upstream circulation path of the content supply piping 7, which includes the upstream piping portion 7a passing through the heat sterilization portion 18 and the upstream feedback path 6a extending from the manifold valve 8, the cleaning liquid may be heated to a temperature required for sterilization of the inside of the content supply piping 7 from the start of CIP or during CIP, and SIP for sterilizing the inside of the upstream piping portion 7a may be performed by circulating the heated cleaning liquid in the content supply piping.

The overall heat transfer coefficient of the second-stage heating portion 13 is calculated during CIP of the upstream circulation path, and when the overall heat transfer coefficient reaches the target value CIP can be stopped and the process proceeds to the next step. Therefore, CIP need not be performed for an unnecessarily long time and can be efficiently performed.

When the cleaning liquid is flowing in the upstream piping portion 7a, a plurality of temperatures measured at predetermined time intervals by the temperature sensors 10 arranged at locations in the upstream piping portion 7a is transmitted to the controller 17 at regular time intervals. The controller 17 selects the lowest temperature from the temperatures measured at a time and calculates the F value. Since the controller 17 selects the lowest temperature, the selected temperature is not always the temperature from the same temperature sensor 10. The temperature sensors 10 measure temperature and transmit the temperature to the controller 17 at predetermined time intervals, and the location where the temperature is the lowest of the measured temperatures is not always the same location.

The controller 17 accumulates the calculated F values for the lowest temperature, and when the accumulated F value reaches the target value, the controller 17 indicates to complete the sterilization step, which is SIP of the inside of the upstream piping portion 7a.

Although the present disclosure is configured as described above, the present disclosure is not limited to the embodiment described above, and various modifications can be made without departing from the spirit of the present disclosure. The container to be filled with a content by the aseptic filling machine is not limited to the bottle, the aseptic filling machine can fill cups, trays or cans with a content, for example. Furthermore, the material of the container is not limited to plastics and may be any material such as a composite of paper and plastics, glass or metal.

REFERENCE SIGNS LIST 2 filler
6 feedback path
6a upstream feedback path
6b downstream feedback path
7 content supply piping
7a upstream piping portion
10 temperature sensor
17 controller
18 heat sterilization portion
21 heating medium line
24 flowmeter

The invention claimed is:

1. A cleaning and sterilizing method for an aseptic filling machine, the aseptic filling machine including content supply piping for feeding a content to an inside of a filler via a heat sterilization portion,
wherein CIP (Cleaning In Place) for cleaning an inside of the content supply piping is performed by circulating a cleaning liquid for cleaning the inside of the content supply piping in the content supply piping,
SIP (Sterilizing In Place) for sterilizing the inside of the content supply piping is performed by heating the cleaning liquid to a required temperature for sterilization of the inside of the content supply piping from a start of the CIP or during the CIP and circulating the heated cleaning liquid in the content supply piping,
temperatures of the cleaning liquid at an inlet and an outlet for the cleaning liquid of heating piping of the heat sterilization portion are measured, temperatures of a heating medium at an inlet and an outlet for the heating medium of the heating piping are measured, an overall heat transfer coefficient of the heating piping is calculated based on the temperatures at the inlet and the outlet for the cleaning liquid of the heating piping and the temperatures at the inlet and the outlet for the heating medium of the heating piping, and it is determined that the CIP is completed when the overall heat transfer coefficient calculated reaches a target value,
a plurality of temperatures is measured at predetermined time intervals by a plurality of temperature sensors provided in the content supply piping, a lowest temperature is selected from the measured temperatures at a time, F values are calculated for the selected lowest temperature, the calculated F values are accumulated, and it is determined that the SIP is completed when an accumulated F value reaches a target value, and
the cleaning liquid is discharged after the CIP and the SIP are completed.

2. The cleaning and sterilizing method for an aseptic filling machine according to claim 1, wherein an upstream piping portion of the content supply piping that passes through the heat sterilization portion is provided with an upstream feedback path to form an upstream circulation path, and the cleaning liquid is circulated in the upstream circulation path.

3. An aseptic filling machine including content supply piping for feeding a content to an inside of a filler via a heat sterilization portion, the aseptic filling machine comprising:
a cleaning liquid supply apparatus that supplies a cleaning liquid for cleaning an inside of the content supply piping to the inside of the content supply piping,
a circulation path for circulating the cleaning liquid supplied in the content supply piping, the circulation path being configured so that SIP (Sterilizing In Place) for sterilizing the inside of the content supply piping is performed by heating the cleaning liquid to a required temperature for sterilization of the inside of the content supply piping from a start of CIP (Cleaning In Place) or during the CIP of the inside of the content supply piping, which is performed using the cleaning liquid being circulated, and circulating the heated cleaning liquid in the content supply piping,
temperature sensors that measure temperatures of the cleaning liquid at an inlet and an outlet for the cleaning liquid of heating piping of the heat sterilization portion,
temperature sensors that measure temperatures of a heating medium at an inlet and an outlet for the heating medium of the heating piping,
a plurality of temperature sensors in the content supply piping,
a controller, the controller being configured to calculate an overall heat transfer coefficient of the heating piping based on the temperatures at the inlet and the outlet for the cleaning liquid of the heating piping and the measured temperatures at the inlet and the outlet for the heating medium of the heating piping, determine that the CIP is completed when the overall heat transfer coefficient calculated reaches a target value, select a lowest temperature from a plurality of measured temperatures at predetermined time intervals by the plurality of temperature sensors, calculate F values for the selected lowest temperature, accumulate the calculated F values, determine that the SIP is completed when an accumulated F value reaches a target value, and indicate to discharge the cleaning liquid after the CIP and the SIP are completed.

4. The aseptic filling machine according to claim 3, wherein an upstream piping portion of the content supply piping that passes through the heat sterilization portion is provided with an upstream feedback path to form an upstream circulation path, and the upstream circulation path is configured so that the cleaning liquid is circulated in the upstream circulation path.

* * * * *